United States Patent [19]

Wegman et al.

[11] Patent Number: 5,053,380

[45] Date of Patent: Oct. 1, 1991

[54] CU-AL CATALYST FOR HYDROGENATION

[75] Inventors: Richard W. Wegman; David R. Bryant, both of South Charleston, W. Va.

[73] Assignee: Union Carbide Chemicals and Plastics Technology Corporation, Danbury, Conn.

[21] Appl. No.: 454,457

[22] Filed: Dec. 21, 1989

[51] Int. Cl.$^5$ .................. B01J 21/04; B01J 23/72
[52] U.S. Cl. ............................................. 502/346
[58] Field of Search ........................................ 502/346

[56] References Cited

U.S. PATENT DOCUMENTS

| | | | |
|---|---|---|---|
| 1,813,953 | 7/1931 | Reppe | 568/405 |
| 2,109,844 | 3/1938 | Lazier | 568/885 |
| 2,110,483 | 3/1938 | Guyer | 260/156 |
| 2,201,235 | 5/1940 | Lenth et al. | 502/346 X |
| 2,290,439 | 7/1942 | Lenth et al. | 260/635 |
| 2,297,769 | 10/1942 | Ipatieff et al. | 502/346 X |
| 2,586,535 | 2/1952 | Ipatieff et al. | 260/667 |
| 2,627,506 | 2/1953 | Hunter et al. | 502/346 |
| 2,895,920 | 7/1959 | Janoski | 502/234 |
| 3,267,157 | 8/1966 | Miya | 568/885 |
| 3,420,901 | 1/1969 | Schulz | 260/659 |
| 3,767,595 | 10/1973 | Montgomery | 502/244 |
| 3,790,505 | 2/1974 | Casey et al. | 252/463 |
| 3,896,053 | 7/1975 | Broecker et al. | 252/466 J |
| 3,933,930 | 1/1976 | Dougherty et al. | 260/635 D |
| 4,009,124 | 2/1977 | Laurer et al. | 252/463 |
| 4,048,196 | 9/1977 | Broecker et al. | 260/346.11 |
| 4,144,198 | 3/1979 | Miya et al. | 252/466 J |
| 4,209,424 | 6/1980 | LeGoff et al. | 252/474 |
| 4,250,111 | 2/1981 | Seale et al. | 564/129 |
| 4,252,689 | 2/1981 | Miya | 252/466 J |
| 4,278,567 | 7/1981 | Miya | 252/466 J |
| 4,279,781 | 7/1981 | Dienes et al. | 252/463 |
| 4,393,251 | 7/1983 | Broecker et al. | 568/811 |
| 4,450,245 | 5/1984 | Adair et al. | 502/211 |
| 4,480,122 | 10/1984 | Horlenko et al. | 560/239 |
| 4,584,419 | 4/1986 | Sharif et al. | 568/864 |
| 4,593,015 | 6/1986 | Hardman et al. | 502/303 |
| 4,600,704 | 7/1986 | Jennings | 502/318 |
| 4,762,817 | 8/1988 | Logsdon et al. | 502/329 |

FOREIGN PATENT DOCUMENTS

| | | |
|---|---|---|
| 0074193 | 3/1983 | European Pat. Off. |
| 0143634 | 6/1985 | European Pat. Off. |
| 55-31428 | 3/1980 | Japan |
| WO83/03409 | 10/1983 | PCT Int'l Appl. |
| 2150550A | 7/1985 | United Kingdom |

Primary Examiner—W. J. Shine
Attorney, Agent, or Firm—Gerald L. Coon

[57] ABSTRACT

A process for hydrogenating bound oxygen-containing organic feeds into their corresponding alcohols by contact with a coprecipitated copper-aluminum catalyst that has been activated by contact with reducing gas at a temperature that gradually increases.

1 Claim, No Drawings

CU-AL CATALYST FOR HYDROGENATION

FIELD OF THE INVENTION

The invention relates to a process for the catalytic vapor phase hydrogenation of bound oxygen-containing organic compounds and particularly to the catalytic hydrogenation of esters.

DESCRIPTION OF RELATED TECHNOLOGY

The hydrogenation of, for example, mono-esters normally yields alcohols according to a simple relationship:

$$RC(O)OR' + 2H_2 \rightarrow R'OH + RCH_2OH$$

The hydrogenation of diesters generally results in a more complicated product mixture. For example, the hydrogenation of a dialkyl maleate typically results in the formation of several products, the amount of each depending on the reaction conditions:

$$ROC(O)CH=CHC(O)OR + xH_2 \rightarrow 2ROH + 1,4\text{-Butanediol} + \text{Tetrahydrofuran} + \text{gamma-Butyrolactone}$$

The concentrations of each of the products are a function of the equilibrium reaction conditions, e.g. temperature, pressure, liquid hourly space velocity (LHSV), and gas hourly space velocity (GHSV) of the process. Like most hydrogenation reactions, the processes are usually catalyzed and are affected strongly by the composition of the catalyst used in the process. Typical hydrogenation catalysts for esters are a combination of reduced copper and zinc (GB 2,150,560 and WO 83/03409) or reduced copper-chromite (U.S. Pat. Nos. 2,100,483; 3,767,595; and 4,584,419). Various promoters can be added as disclosed in U.S. Pat. No. 2,109,844 (barium or cadmium).

U.S. Pat. Nos. 2,297,769; 4,209,424; 4,593,015; and 4,600,704 and EP 0143,634 discuss particular reduction activation processes—for copper-based catalysts.

In EP 143,634 the vapor phase hydrogenation of diethyl maleate is reported. The hydrogenation reaction is carried out with a copper-chromite catalyst at 170°–190° C. and approximately 450 psig. It is disclosed that controlled reduction of the catalyst is necessary to ensure high catalyst activity. The reduction process involves a rapid heating directly to a reduction temperature of and maintaining that temperature more or less constant over the entire reduction period.

SUMMARY OF THE INVENTION

It is an objective of the invention to provide an activated, copper-based catalyst for the hydrogenation of bound oxygen-containing organic compounds.

It is another objective to provide a process that results in an active, selective catalyst and a hydrogenation process using such a catalyst. Other objectives will become apparent from the description contained herein.

In accordance with the invention, the invention comprises an active hydrogenation catalyst composition produced by reducing a homogenous mixture of copper and aluminum oxides by heating in the presence of a reducing gas under activation conditions which comprise reduction temperature that gradually increases from a starting temperature of about 40° to 75° C. to a final temperature of about 150° C. to 250° C. The resulting catalyst is useful for catalyzing the vapor phase hydrogenation of bound oxygen-containing organic compounds, in general, and esters, in particular to produce various hydrogenated products such as alcohols. For example, the catalyst of the present invention can be used to hydrogenate diethyl maleate to produce a hydrogenated product containing inter alia, such desired products as ethanol, tetrahydrofuran, 1,4-butanediol and gamma-butyrolactone.

The process according to the invention produces catalysts that provide high rates of conversion with control over the distribution of products.

DETAILED DESCRIPTION OF THE INVENTION

The catalyst of the invention, which is useful in the inventive process, is an activated combination of copper and aluminum. The weight ratio of Cu:Al in the catalyst can vary widely. Active catalysts may have a weight ratio of Cu:Al of about 90:10 to about 10:90 when calculated as the elemental forms of each. More preferably, the catalyst has a weight ratio of copper to aluminum of between about 75:25 to about 25:75.

The catalyst is made by the controlled reduction of a catalyst precursor containing a more or less homogeneous mixture of the oxides of copper and aluminum. The catalyst precursor can be made by coprecipitating copper and aluminum from any of their water soluble salts in the desired weight ratio and/or by mixing finely divided oxides of copper and aluminum. Coprecipitation is preferred. Suitable water soluble salts include, inter alia, the chlorides, sulfates, lactates and nitrates of copper and aluminum. Preferred are the nitrate salts of each component. Coprecipitation of copper and aluminum can be induced by adding an aqueous solution of sodium carbonate to the solution of the copper and aluminum salts. The precipitated salts are washed, dried to a slightly elevated temperature, e.g., about 80° C. to about 120° C., and calcined in air, e.g., at 350°–450° C. for 1 to 3 hours to yield homogenous oxide catalyst precursors.

Catalyst precursors are transformed into catalysts according to the invention by heating the calcined mixture of copper and aluminum in a reducing atmosphere at a gradually increasing temperature, typically from an initial temperature of between about 40° to 75° C. to a final reduction temperature of between about 150° to 250° C., preferably between about 160° C. and 220° C., and most preferably from an initial temperature of about 50° C. to a final temperature of about 180° C. The temperature is gradually increased, normally by increasing the temperature of the reducing atmosphere, at a positive rate of normally less than about 24° C./hr (0.4° C./min), preferably at a rate of about 3°–18° C./hr (about 0.05°–0.3° C./min.), and most preferably at a rate of about 3°–6° C./hr (0.05°–0.1° C./min). The heating rate and conditions normally are chosen to produce a catalyst composition having a high activity to maximize hydrogenation efficiency, e.g., the formation of alcohols. However, in certain instances, as may be encountered when hydrogenating diesters, such as dialkyl maleates, it may be desired to optimize the reduction conditions to produce a catalyst that favors one or more hydrogenation product relative to others. For example, in the case of hydrogenating diethyl maleate, reduction conditions may be selected to provide a catalyst that favors the production of tetrahydrofuran, or gamma-butyrolactone relative to ethanol or 1,4-butanediol.

The heating rate should be chosen to minimize or avoid the generation of an exothermic temperature rise which can result during the reduction of Cu-Al catalysts. See, U.S. Pat. Nos. 2,297,769; 4,209,424; 4,593,015; and 4,600,704 all of which are incorporated herein by reference.

The reduction process according to the invention can be monitored to avoid an exotherm by comparing the rate of actual temperature rise in the catalyst bed to the temperature increase rate that would occur in the absence of any exothermic reduction as a consequence of the heating rate applied with external means, e.g. heated reducing gas, resistance heaters around and/or throughout the catalyst bed, etc.

If desired, a variable rate of temperature increase, obtained for example by combining different temperature increase rates within the ranges identified above, also can be used to produce a catalyst according to the invention, e.g., the precursor can be reduced by initially increasing the temperature at a rate of 0.06° C./hr for 2 hours followed by a further reduction at a temperature which increases at the rate of about 0.5° C./hr for 3 hours, etc.

Exemplary reducing gases include hydrogen, carbon monoxide, and mixtures thereof in addition to other reducing gases known to those in this art. The reducing gas can be supplied a pressure of about 1-20 atm. and may be supplied in admixture with an inert gas. If an inert gas is used, the reducing gas to inert gas volumetric ratio can be about 0.1:20 to about 10:1. Suitable inert gases include, inter alia, nitrogen, argon, and methane. The GHSV in the reduction step can be within the range of about 100 to about 100,000 per hour.

The length of the reduction period depends upon the initial reduction temperature, the final reduction temperature, and the rate of temperature increase. Generally, reduction (activation) of the precursor catalyst is done over a period of about 12 to 48 hours. The resulting catalyst is useful for catalyzing the hydrogenation of bound oxygen-containing organic compounds and particularly esters to produce a variety of hydrogenated products, particularly alcohols.

A variety of organic feeds containing bound oxygen may be hydrogenated using the reduced copper-aluminum catalysts of the invention. Suitable feeds include: (1) aromatic and nonaromatic (aliphatic and alicyclic carboxylic acids having more than one carbon atom per carboxyl group), esters of monobasic acids exemplified by acetic, propionic, butyric, caprylic, lauric, capric, myristic, palmitic, linoleic, oleic, ricinoleic, stearic, hexahydrobenzoic and hexahydrotoluic acids; (2) esters of nonaromatic, dibasic and polybasic acids exemplified by hexahydrophthalic, azelaic, sebacic, succinic, suberic, pimelic, nonanedicarboxylic, decamethylenedicarboxylic, brassylic, and adipic acids, dodecamethylenedicarboxylic, and hexadecamethylenedicarboxylic acids; (3) esters of hydroxy, aldehydic, and ketonic acids, e.g. lactic, ricinoleic, tartaric, and pyruvic acids; (4) mixtures of esters such as those listed above or obtained as a result of the saponification of a fat such as coconut oil; (5) esters of hydroaromatic acids; (6) mono- and dialkyl oxalates; (7) mono-esters, di-esters, and mixtures thereof; and (8) straight or branched chain, saturated or unsaturated aldehydes containing from 2 to about 22 carbon atoms.

The general formula for mono-esters that can be hydrogenated according to the invention is $R^1C(O)OR^2$ where $R^1$ and $R^2$ may be the same or different and represent aliphatic groups having from 1 to 22 or more carbon atoms. Exemplary mono-esters are methyl acetate, butyl acetate, and methyl propionate. Suitable di-esters have the general formula $R^3OC(O)R^4C(O)OR^5$. $R^3$ and $R^5$ have the same definitions as for $R^1$ and $R^2$ above. $R^4$ is the bridge between the two ester groups and can be a saturated or unsaturated hydrocarbon moiety having from 1 to 10 or more carbon atoms. Exemplary di-esters that can be hydrogenated according to the invention include esters having up to about 16 or more carbon atoms of primary or secondary alcohols, e.g. dialkyl maleates and dialkyl succinates. Mono-esters and di-esters may be hydrogenated individually or in combination.

As noted above, the catalyst of the present invention can also be used for hydrogenating a wide variety of straight or branched chain, saturated or unsaturated aldehydes containing from 2 to 22 carbon atoms. The range of useful feed stocks is limited only by the practicality of vaporizing the higher boiling aldehydes. Any technique that can vaporize the aldehyde is useful for extending the range of feed stocks for hydrogenation with the catalysts according to the invention. Suitable aldehydes include saturated aldehydes like acetaldehyde, propionaldehyde, iso-butyraldehyde, n-butyraldehyde, isopentyl aldehyde, 2-methylpentaldehyde, 2-ethylhexaldehyde, 2-ethylbutyraldehyde, n-valeraldehyde, iso-valeraldehyde, caproaldehyde, iso-hexaldehyde, caprylaldehyde, n-nonylaldehyde, n-decanal, dodecanal, tridecanal, myristic aldehyde, pentadecaldehyde, palmitic aldehyde, stearic aldehyde and such unsaturated aldehydes as acrolein, methacrolein, ethacrolein, 2-ethyl-3-propylacrolein, crotonaldehyde and the like. The aldehyde may be in a substantially pure state or mixed with a component or components other than the aldehyde itself. Furthermore, a mixture of aldehydes may be employed.

The aldehyde or mixture of aldehydes employed may be obtained by an oxo process. Either a portion or all of the product mixture of an oxo process, i.e., the reaction of olefins with carbon monoxide and hydrogen in the presence of a catalyst to add a carbonyl group at one of the carbon atoms of the olefinic group, can be used. Of course, the aldehyde or mixture of aldehydes can be obtained by processes other than the oxo process such as by oxidation of olefins or saturated hydrocarbons or by an aldol condensation. The present invention is not limited to the source of any particular aldehyde or other bound oxygen-containing compound.

In accordance with the process of the present invention, the bound oxygen-containing, organic compound feed in a vaporous state is brought into contact with the hydrogenation catalyst in the presence of a reducing gas, e.g., hydrogen-containing gas. Although substantially pure hydrogen can be used, it is preferable in some cases to provide the hydrogen to the reaction in admixture with other gases, desirably inert to the feed and catalyst. Suitable inert gases for mixing with hydrogen are nitrogen, methane, and argon. The term "hydrogen-containing gas" includes both substantially pure hydrogen gas as well as gaseous mixtures containing hydrogen.

While the concentration of hydrogen in the reaction zone is not critical, generally there should be an excess of hydrogen over the stoichiometric requirement relative to the organic feed to be hydrogenated. The mole ratio of hydrogen to organic feed will usually be from about 5 to about 400 and preferably from about 10 to 200.

The process of the present invention preferably is carried out in a continuous manner. In the preferred method of continuous operation, the organic feed or the mixture of organic feeds are vaporized as needed and brought together with the hydrogen-containing gas at the desired temperature and pressure in the presence of the catalyst of the present invention.

An inert diluent, such as an aliphatic hydrocarbon, may be fed into the hydrogenation reactor along with the organic feed being hydrogenated. Alkanes such as pentane or hexane are examples of suitable diluents. The volumetric ratio of organic feed, e.g., ester, to diluent may vary with the reactor system but can typically be within about 0.5 to about 4. Other ratios may be used both above and below this range.

The catalyst advantageously may be used in a fixed, fluidized, ebullating, or moving catalyst bed reactor. Preferably, a fixed bed is used in an elongated tubular reactor having the catalyst supported within the tubes. Adiabatic tank type reactors also can be used. In such reactors, the heat of reaction causes an increase in reaction temperature from reactor inlet to reactor outlet.

The hydrogenation may be effected at a temperature of about 100°–300° C., at a pressure of about 200–2000 psig, about 0.1–10/hr LHSV, and about 1,000–50,000/hr GHSV. Preferably, the reaction is conducted at a temperature of 120°–260° C., at a pressure of less than about 600 psig, and about 0.1–4/hr LHSV. In view of the need to maintain the organic reactant feeds and reaction products (typically alcohols) in the vaporous state and above their dew points, the chosen reaction pressure is influenced somewhat by the reaction temperature, the nature of the organic feed undergoing hydrogenation and the quantity of hydrogen-containing gas. Optimizing these factors to operate the process in the vapor phase is within the ordinary skill level existing in this art. The hydrogenation may be effected in one or more stages.

As used herein, LHSV refers to the volumetric feed rate of the organic feed component passed to the catalyst bed as a liquid divided by the unit volume of catalyst of the bed. In a parallel definition, GHSV refers to the volumetric feed rate of all gas or vapor components fed to the catalyst bed at standard temperature and pressure divided by the unit volume of the catalyst bed.

Appropriate organic feeds and processing sequences for use with the invention are set forth in U.S. Pat. Nos. 4,172,961; 4,032,458; 2,079,414; 4,112,245; 4,584,419; and 4,762,817 the disclosures of which are herein incorporated by reference.

The following examples are presented to illustrate the invention: the examples are not intended to limit the scope of the invention as set forth in the appended claims.

EXAMPLES

Preparation of Catalyst Precursors

An active hydrogenation catalyst according to the invention is made by first preparing a precursor catalyst composition. The catalyst precursor then is subject to an activation (reduction) treatment under carefully controlled conditions in accordance with the present invention.

A precursor catalyst can be prepared by dissolving copper nitrate and aluminum nitrate in deionized water at 25° C. The solution of metal salts and a separate solution of sodium carbonate are individually heated to about 45°–75° C. The carbonate solution is quickly added to the nitrate solution with rapid stirring to produce a precipitate. The precipitated mixture is stirred while cooling to 25° C. The precipitate is isolated, washed with deionized water, dried in air at a slightly elevated temperature, e.g. about 80° C. to about 120° C., and then calcined in air at about 300° to about 550° C. The resulting material which comprises the hydrogenation catalyst precursor is pressed into pellets and crushed into particles of about 30–40 mesh. It is to be understood that the drying step may be combined with the calcination step if desired.

For example, a Cu(54):Al(46) catalyst precursor may be prepared in the following manner. A first solution (Solution A) is prepared by dissolving $Cu(NO_3)_2.3H_2O$ (10.2 g) and $Al(NO_3)_3.9H_2O$ (39.22 g) in 200 mL deionized water (25° C.). A second solution (Solution B) is prepared by dissolving $Na_2CO_3$ (30 g) in 100 mL deionized water (25° C.). Solutions A and B are heated to 60° C. Solution B is then quickly added with rapid stirring to Solution A resulting in formation of a precipitate. This mixture is stirred for 3 hr. while cooling to 25° C. The precipitate is isolated and washed with 1000 mL of deionized water (25° C.). The precipitate then is dried in the air at 100° C. for 18 hr and calcined in air at 400° C. for 2 hr. The resulting material which constitutes the catalyst precursor can be pressed into pellets and crushed into particles in the 30/40 mesh range. Other compositions can be made similarly.

The hydrogenation catalyst precursors used in the following examples were made using substantially the same process by simply changing the relative amounts of the various ingredients.

Reduction and Hydrogenation Procedures

The precursor catalysts made in this manner then are reduced in accordance with the present invention. Unless otherwise stated in the examples which follow, the following standard process conditions were used to activate the precursor catalysts. Under these conditions 0.5 or 1 cc of (unreduced) precursor catalyst is loaded into the rear third of a stainless steel reaction tube. The reaction tube is a U-tube design where the first two-thirds of the tube is packed with inert glass beads. This front section serves as a gas and liquid preheater. The precursor catalyst is activated in situ with a mixture of 0.5% hydrogen in nitrogen at a standard GHSV of 1800/hr, at an initial temperature of about 50° C. with the temperature gradually increased at a rate of between 0.05° C./min (3° C./hr) to 0.1° C./min (6° C./hr) to a final temperature of about 180° C. in an oven equipped to handle four reaction tubes.

Once activated, the gas flow is switched to pure hydrogen, and the pressure and flow rate are adjusted to the desired hydrogenation conditions. Unless otherwise stated in the following examples, the following standard hydrogenation conditions were used. The liquid feed rate of the ester together with hexane as a diluent is adjusted to a LHSV of 0.6/hr. The diluent ratio is typically 1:1 by volume for the examples. Due to the preheater section, the ester feed is vaporized and contacts the catalyst as a vapor.

The standard hydrogenation reaction conditions are set at a temperature of 220° C., at a pressure of 450 psig and at a GHSV of 15,000/hr at which they are maintained for 20 hours. During the last 4 hours, the hydrogenation products are collected by passing the reactor effluent through a series of condensation traps containing isopropanol and maintained at 0° to −75° C. The products are analyzed with a capillary gas chromatograph using a 30 mm×0.32 mm capillary. The products in the examples are reported in terms of weight percent and exclude any isopropanol or inert diluent.

Table 1, and succeeding tables associated with the subsequent examples, report the weight percent of various components in the hydrogenated product stream including ethanol (EtOH), tetrahydrofuran (THF), butanol (BuOH), gamma-butyrolactone (g-BL), 1,4-butanediol (BD) and diethyl succinate (DES). The level of DES in the hydrogenation product provides an indication of catalyst activity. Lower levels of DES in the hydrogenation product indicate higher hydrogenation activities for the catalysts.

EXAMPLES 1-8

These examples demonstrate that the method used to activate a catalyst can have a marked impact on catalyst performance. The catalysts were obtained by activating precursor catalysts both according to the invention and according to the procedure outlined in EP 143,634 for a copper-chromite catalyst. In Examples 1-3 and 5-7, the precursor catalysts were heated at a low, constant rate of heating to cause the catalyst temperature to increase gradually over the range 50°-180° C. in the presence of a reducing atmosphere of 1% $H_2$ in $N_2$. Examples 4 and 8 illustrate the EP procedure where the precursor catalyst is rapidly heated (10 min) to a temperature of 150° C. under an atmosphere of 0.5% $H_2/N_2$ and maintained at 150° C. for 22 hr. The listed time is the time required to traverse the 50°-180° C. temperature range at the given heat rate.

Table 1 presents the results of hydrogenating diethylmaleate at standard conditions illustrating the effects of varying the catalyst heat rate during activation (reduction) on catalyst performance. The weight ratio of the catalyst elements is shown in parentheses.

TABLE 1

Various Reduction Procecures

| Example | Catalyst | Heat[1] Rate | Time[2] | EtOH | THF | Products g-BL | BD | DES |
|---|---|---|---|---|---|---|---|---|
| 1 | Cu(70):Al(30) | 0.3 | 7.2 | 28.2 | 25.8 | 8.2 | 0.2 | 34.9 |
| 2 | Cu(70):Al(30) | 0.1 | 21.6 | 36.0 | 36.1 | 7.4 | 0.0 | 18.8 |
| 3 | Cu(70):Al(30) | 0.05 | 43.3 | 52.8 | 1.5 | 29.4 | 11.0 | 2.6 |
| 4 | Cu(70):Al(30) | EP | — | 31.9 | 30.9 | 7.1 | 0.8 | 27.7 |
| 5 | Cu(54):Al(46) | 0.3 | 7.2 | 38.3 | 1.5 | 26.6 | 9.8 | 22.3 |
| 6 | Cu(54):Al(46) | 0.1 | 21.6 | 53.3 | 2.6 | 29.1 | 11.5 | 0.5 |
| 7 | Cu(54):Al(46) | 0.05 | 43.3 | 50.1 | 34.6 | 3.3 | 0.1 | 7.7 |
| 8 | Cu(54):Al(46) | EP | — | 47.7 | 1.8 | 32.4 | 11.4 | 4.5 |

[1] °C./min over the range 50°-180° C. EP reduction procedure: the catalyst is heated in 10 min to 150° C. and maintained at 150° C. for 22 hrs.
[2] Time in hours to traverse 50°-180° C.

Table 1 illustrates the effects of heating rate on the catalyst activity and selectivity relative to the constant-temperature reduction process of EP 143,634. The Cu(70):Al(30) catalyst did not exhibit its best activity at the same heating rate as the Cu(54):Al(46) catalyst. Based on the amount of undesirable DES in the product mixture, the most desirable catalysts of Examples 3 and 6 according to the invention have a more desirable product mixture than the catalysts of examples 4 and 8.

EXAMPLES 9 to 11

These examples illustrate the effect of varying the $H_2/N_2$ GHSV while maintaining a constant reduction heating rate.

The catalyst precursors were reduced at a heating rate of 0.1° C./min between 50° and 180° C. while varying the GHSV of the reduction gas (1% $H_2$ in $N_2$) from 600 to 5400 $hr^{-1}$. The activated catalysts were screened using diethylmaleate as the ester feed at standard hydrogenation conditions. The results are reported in Table 2.

It is theorized that if left uncontrolled, the exothermic heat of the reduction reaction can drive the reaction forward too quickly and adversely affect the subsequent performance of the reduced catalyst. The evolution of heat is thought to act according to the following relationship.

$$CuO + H_2 \rightarrow Cu^\circ + H_2O + Heat$$

TABLE 2

Effect of Reduction Gas GHSV on Catalyst Activity

| Example | Catalyst | GHSV[1] | Heat Rate | EtOH | THF | Products[2] g-BL | BD | DES |
|---|---|---|---|---|---|---|---|---|
| 9 | Cu(54):Al(46) | 600 | 0.1 | 46.5 | 1.7 | 29.9 | 17.4 | 3.3 |
| 10 | Cu(54):Al(46) | 1800 | 0.1 | 53.3 | 3.6 | 29.1 | 11.5 | 0.5 |
| 11 | Cu(54):Al(46) | 5400 | 0.1 | 61.8 | 3.1 | 23.6 | 7.9 | 1.1 |

[1] $H_2/N_2$ space velocity during reduction ($hr^{-1}$)
[2] All hydrogenation runs: GHSV = 15000/hr
Temperature = 220° C.
Pressure = 450 psi From Table 2, the flow rate of the gas used in the reduction step appears to have an effect on the activity level of the resulting catalyst. The preferred combination of reduction gas flow rate and heating rate for activating a particular precursor catalyst can be determined by one skilled in this art with no more than routine experimentation.

Comparative Examples 1-4

Nonhomogeneous Cu-Al catalysts were prepared by impregnating alumina ($Al_2O_3$) with various amounts of copper. In comparative Examples 1, 3, and 4, the heterogeneous catalysts were made by impregnating $Al_2O_3$ with an aqueous solution of copper nitrate. In comparative Example 2, the catalyst was prepared by the well-known incipient wetness technique. These comparative catalysts were reduced at a temperature that was gradually increased over the range of 50°–180° C. at a rate of 0.1° C./min. Diethyl maleate was hydrogenated in the presence of the reduced, nonhomogeneous catalysts under the standard conditions of 220° C., 450 psig, and GHSV of 15,000/hr. Results are shown in Table 3.

TABLE 3

| Comparative Example | Catalyst (Cu:Al) | Products | | | | | |
|---|---|---|---|---|---|---|---|
| | | EtOH | THF | BuOH | g-BL | BD | DES |
| 1 | 25:75 | 6.2 | 0.8 | 0.1 | 4.8 | 0.0 | 87.1 |
| 2 | 25:75 | 1.1 | 0.0 | 0.0 | 0.0 | 0.0 | 98.5 |
| 3 | 50:50 | 19.6 | 3.6 | 0.1 | 11.2 | 0.4 | 64.3 |
| 4 | 70:30 | 51.2 | 1.2 | 0.8 | 23.0 | 18.4 | 4.8 |

In general, non-homogeneous catalysts prepared by supporting copper on alumina are inferior to the homogeneous Cu-Al catalysts (e.g. prepared by co-precipitation) because they result in a product mixture high in undesirable DES and low in desired 1,4-butanediol, gamma-butyrolacone, or THF.

EXAMPLES 12–16

Cu-Al catalysts prepared in accordance with the present invention were utilized in the hydrogenation of dibutylmaleate (DBM). The catalysts were prepared by co-precipitation and activated under a gradually increasing temperature over the temperature range of 50°–180° C. at a rate of 0.1° C./min for Examples 12 and 14 and a rate of 0.05° C./min for Examples 13, 15, and 16. The hydrogenation reactions were carried out at the standard conditions of 220° C., 450 psig, and a GHSV of 15,000/hr. The results are reported in Table 4.

TABLE 4

| Example | Catalyst | LHSV/hr. | THF | BuOH | g-BL | BD | DBM |
|---|---|---|---|---|---|---|---|
| 12 | Cu(44):Al(56) | 0.3 | 1.2 | 70.4 | 21.6 | 5.5 | 0.0 |
| 13 | Cu(44):Al(56) | 0.6 | 1.2 | 76.6 | 17.9 | 2.5 | 0.0 |
| 14 | Cu(44):Al(56) | 1.2 | 0.4 | 69.1 | 19.0 | 6.7 | 3.9 |
| 15 | Cu(54):Al(46) | 1.2 | 1.5 | 69.8 | 21.2 | 6.0 | 0.1 |
| 16 | Cu(70):Al(30) | 1.2 | 24.4 | 63.5 | 5.8 | 0.1 | 3.3 |

KEY: DBM = unreacted dibutyl maleate.

EXAMPLES 17–18

Hydrogenation of butyl acetate (BuOAc) was carried out. The desired products are ethanol and n-butanol according to the following reaction:

$$CH_3C(O)OCH_2CH_2CH_2CH_3 + H_2 \rightarrow CH_3CH_2OH + CH_3CH_2CH_2CH_2OH$$

The results are reported below in Table 5. The precursor catalysts were reduced using the standard conditions. The hydrogenating reactions were run at the standard hydrogenating conditions of 220° C., 450 psig and a GHSV of 15,000/hr.

TABLE 5

| Example | Catalyst | LHSV (hr$^{-1}$) | Products (wt %) | | |
|---|---|---|---|---|---|
| | | | EtOH | BuOH | BuOAc |
| 17 | Cu(44):Al(56) | 0.6 | 35.1 | 63.4 | 0.06 |
| 18 | Cu(44):Al(56) | 1.2 | 32.3 | 63.1 | 0.5 |

BuOAc = Unreacted butyl acetate

These results demonstrate that mono-esters are readily hydrogenated with Cu-Al catalysts of the present invention.

EXAMPLES 19–22

Cu-Al catalyst precursors of various compositions were prepared according to the above-described procedure. The precursor catalysts were reduced over the temperature range 50°–180° C. at the heat rate shown in Table 6 below. Hydrogenation of diethyl maleate was carried out using the standard hydrogenation conditions. The results are reported below in Table 6.

TABLE 6

| Example | Catalyst | Heat Rate[1] | Products (wt. %) | | | | | |
|---|---|---|---|---|---|---|---|---|
| | | | ETOH | THF | BuOH | g-BL | 1,4-BD | DES |
| 19 | Cu(28)Al(72) | 0.05 | 28.9 | 12.0 | 0.1 | 11.0 | 0.3 | 42.0 |
| 20 | Cu(44)Al(56) | 0.1 | 43.8 | 29.5 | 0.2 | 6.3 | 0.1 | 17.7 |
| 21 | Cu(54)Al(46) | 0.1 | 56.6 | 2.2 | 0.7 | 21.9 | 17.2 | 0.2 |
| 22 | Cu(70)Al(30) | 0.05 | 50.1 | 34.6 | 0.2 | 3.3 | 0.1 | 7.7 |

[1]°C/min

EXAMPLES 23–24

A Cu(46)Al(56) catalyst prepared and activated using the standard procedures was examined for its performance when hydrogenating diethyl maleate using the standard hydrogenation conditions except that the LHSV was varied between 0.3/hr and 0.5/hr. The results are reported below in Table 7.

TABLE 7

| Example | Catalyst | LHSV[1] | Products Approximate Weight Percent | | | | | |
|---|---|---|---|---|---|---|---|---|
| | | | ETOH | THF | BuOH | g-BL | BD | DES |
| 23 | Cu(44):Al(56) | 0.3 | 53.9 | 43.0 | 0.6 | 0.0 | 0.0 | 0.0 |
| 24 | Cu(44):Al(56) | 0.5 | 54.1 | 40.9 | 0.3 | 0.8 | 0.0 | 0.3 |

[1]hr$^{-1}$

EXAMPLES 25–29

The Cu(54)Al(46) catalyst of the above examples (23 and 24) was examined further at various hydrogenation operating conditions. The results are presented below in Table 8.

TABLE 8

| Example | LHSV[1] | temp[2] | psi | GHSV[1] | ETOH | THF | BuOH | g-BL | BD | DES |
|---|---|---|---|---|---|---|---|---|---|---|
| 25 | 0.3 | 220 | 450 | 15000 | 45.9 | 3.3 | 0.8 | 19.8 | 29.1 | 0.1 |
| 26 | 0.6 | 220 | 450 | 10000 | 61.1 | 2.4 | 0.5 | 27.7 | 7.4 | 0.3 |
| 27 | 0.6 | 220 | 450 | 20000 | 47.6 | 1.3 | 0.4 | 26.6 | 20.6 | 2.9 |
| 28 | 0.6 | 220 | 600 | 15000 | 62.4 | 2.5 | 0.6 | 20.6 | 12.8 | 0.3 |
| 29 | 0.6 | 250 | 450 | 15000 | 52.7 | 5.1 | 3.8 | 27.9 | 9.1 | 0.0 |

[1] hr$^{-1}$
[2] °C.

While certain specific embodiments of the invention have been described with particularity herein, it will be recognized that various modifications thereof will occur to those skilled in the art, and it is to be understood that such modifications and variations are to be included within the purview of this application and the spirit and scope of the appended claims.

We claim:

1. A reduced catalyst composition consisting of copper and aluminum made by a process comprising:

coprecipitating copper and aluminum from their water soluble salts to form a precipitate;

drying and calcining the precipitate to form a calcined catalyst; and activating the calcined catalyst by heating said calcined catalyst in the presence of a reducing gas under activation conditions which comprise a reducing temperature that gradually increases from an initial temperature of about 50° C. to a final temperature of about 180° C. and wherein said reducing temperature is gradually increased at a rate of about 3° C. to about 6° C. per hour.

* * * * *